US011446643B2

(12) United States Patent
Morii et al.

(10) Patent No.: US 11,446,643 B2
(45) Date of Patent: Sep. 20, 2022

(54) METHOD FOR PRODUCING CATALYST AND METHOD FOR PRODUCING UNSATURATED NITRILE

(71) Applicant: ASAHI KASEI KABUSHIKI KAISHA, Tokyo (JP)

(72) Inventors: Kazunari Morii, Tokyo (JP); Akiyoshi Fukuzawa, Tokyo (JP); Masatoshi Kaneta, Tokyo (JP)

(73) Assignee: ASAHI KASEI KABUSHIKI KAISHA, Tokyo (JP)

( * ) Notice: Subject to any disclaimer, the term of this patent is extended or adjusted under 35 U.S.C. 154(b) by 74 days.

(21) Appl. No.: 16/630,771

(22) PCT Filed: Jun. 18, 2018

(86) PCT No.: PCT/JP2018/023101
§ 371 (c)(1),
(2) Date: Jan. 13, 2020

(87) PCT Pub. No.: WO2019/012920
PCT Pub. Date: Jan. 17, 2019

(65) Prior Publication Data
US 2021/0146343 A1 May 20, 2021

(30) Foreign Application Priority Data

Jul. 14, 2017 (JP) .............................. JP2017-138362

(51) Int. Cl.
*B01J 23/887* (2006.01)
*B01J 37/08* (2006.01)
*C07C 253/22* (2006.01)
*C07C 253/26* (2006.01)

(52) U.S. Cl.
CPC .......... *B01J 23/8876* (2013.01); *B01J 37/08* (2013.01); *C07C 253/22* (2013.01); *C07C 253/26* (2013.01); *B01J 2523/54* (2013.01); *B01J 2523/68* (2013.01); *B01J 2523/842* (2013.01)

(58) Field of Classification Search
CPC .............. B01J 23/8876; B01J 2523/54; B01J 2523/68; B01J 2523/842; B01J 23/8437; B01J 37/08; B01J 37/086; B01J 37/12; B01J 37/16; B01J 37/20; B01J 37/22; B01J 37/28; C07C 253/22; C07C 253/26
USPC ......... 502/311, 316; 558/318, 319, 323, 324
See application file for complete search history.

(56) References Cited

U.S. PATENT DOCUMENTS 4,414,133 A     11/1983  Otake et al.
6,740,769 B1 *  5/2004   Mizutani .............. B01J 23/8876
                                                           502/110
8,361,923 B2 *  1/2013   Kano .................... C07C 45/35
                                                           502/311
8,877,966 B2 * 11/2014   Herzog ................ B01J 27/198
                                                           562/599
2002/0062042 A1* 5/2002  Chaturvedi ............ C07C 57/04
                                                           562/546
2002/0188150 A1 12/2002  Gaffney et al.
2006/0155139 A1* 7/2006  Yanagi ................... B01J 35/002
                                                           558/322
2011/0166015 A1* 7/2011  Norton ................... B01J 35/04
                                                           502/348
2013/0072710 A1* 3/2013  Brazdil ............... B01J 23/8876
                                                           558/321
2014/0171303 A1* 6/2014  Yoshida .............. B01J 23/8876
                                                           502/304
2015/0238939 A1* 8/2015  Yoshida .................. B01J 23/88
                                                           558/324
2016/0340296 A1 11/2016  Brazdil et al.
2018/0117565 A1  5/2018  Tamura et al.
2018/0222850 A1* 8/2018  Li ........................ B01J 35/1071
2020/0047163 A1  2/2020  Iitsuka et al.
2020/0061590 A1* 2/2020  Tomoda ............... B01J 37/0045

FOREIGN PATENT DOCUMENTS

CN      1172689 A     2/1998
CN      1390642 A     1/2003
CN    102371157 A     3/2012
EP    0 057 918 A2    8/1982
EP    1 223 164 A1    7/2002
JP     58-40149 A     3/1983

(Continued)

OTHER PUBLICATIONS

International Preliminary Report on Patentability, dated Jan. 14, 2020, and English translation of the Written Opinion of the International Searching Authority, for International Application No. PCT/JP2018/023101.
International Search Report for PCT/JP2018/023101 (PCT/ISA/210) dated Sep. 4, 2018.
Written Opinion of the International Searching Authority for PCT/JP2018/023101 (PCT/ISA/237) dated Sep. 4, 2018.

* cited by examiner

Primary Examiner — Patricia L. Hailey
(74) Attorney, Agent, or Firm — Birch, Stewart, Kolasch & Birch, LLP

(57) ABSTRACT

A method for producing a catalyst, including a slurry preparation step of preparing a slurry comprising a Mo compound, an Fe compound, a Bi compound, and an additive having a decomposition temperature of 500° C. or less; a drying step of drying the slurry to obtain a dried material; and a calcination step of calcining the dried material to obtain a calcined material, wherein the calcination step comprises a step of raising temperature of a calcination atmosphere to a predetermined temperature, and a temperature raising rate is 10° C./min or less at least at a temperature equal to or lower than the decomposition temperature of the additive.

7 Claims, No Drawings

(56) References Cited

FOREIGN PATENT DOCUMENTS

| | | |
|---|---|---|
| JP | 2013-17917 A | 1/2013 |
| JP | 2014-531311 A | 11/2014 |
| JP | 2015-157241 A | 9/2015 |
| JP | 2015-157243 A | 9/2015 |
| JP | 2015-188801 A | 11/2015 |
| JP | 2015-188802 A | 11/2015 |
| JP | 2016-120468 A | 7/2016 |
| TW | 201700171 A | 1/2017 |
| WO | WO 2019/187840 A1 | 10/2019 |

METHOD FOR PRODUCING CATALYST AND METHOD FOR PRODUCING UNSATURATED NITRILE

TECHNICAL FIELD

The present invention relates to a method for producing a catalyst and a method for producing an unsaturated nitrile using a catalyst.

BACKGROUND ART

A method for obtaining an unsaturated nitrile such as acrylonitrile or methacrylonitrile by subjecting an olefin such as propylene or isobutene to gas-phase catalytic oxidation by molecular oxygen in the presence of ammonia is widely known as an "ammoxidation process", and currently, the method is widely carried out on an industrial scale.

Various studies on a catalyst for use in the ammoxidation process have been conducted for the purpose of carrying out this process on an industrial scale further efficiently, and a catalyst composed of a composite oxide such as a Mo—Bi—Fe or Fe—Sb composite oxide has been known. For example, Patent Literatures 1 and 2 each disclose a catalyst in which an additional component is added in addition to molybdenum, bismuth, and iron.

CITATION LIST

Patent Literature

Patent Literature 1: Japanese Patent Laid-Open No. 2015-157241
Patent Literature 2: Japanese Patent Laid-Open No. 2015-188802

SUMMARY OF INVENTION

Technical Problem

However, it is considered that the catalysts obtained by the methods described in Patent Literatures 1 and 2 have room for further improvements in terms of catalytic efficiency (reaction product yield).

The present invention has been completed in consideration of the above circumstance, and an object of the present invention is to provide a method for producing a Mo—Bi—Fe catalyst having a high catalytic efficiency (for example, giving a high unsaturated nitrile yield) and a method for producing an unsaturated nitrile using the catalyst.

Solution to Problem

As a method for producing a metal oxide catalyst, a method of preparing a slurry containing a metal compound to be a metal source, and drying and calcining this slurry has been known, and an additive, such as an organic acid, which decomposes at a temperature lower than a calcination temperature is added in the slurry in some cases in order to improve the dispersion state of the metal compound. In the slurry containing a Mo compound, a Bi compound, and an Fe compound, an additive is also added in some cases in order to make the dispersion state of the metals good, and Patent Literatures 1 and 2 also disclose an example where tartaric acid or oxalic acid is added.

The present inventors have conducted diligent studies in order to produce a Mo—Bi—Fe catalyst having a high catalytic efficiency to find that in a case where a catalyst is produced by the method using a slurry containing such an additive having a low decomposition temperature and Mo, Bi, and Fe compounds, an excessively large temperature raising rate until the temperature reaches the decomposition temperature of the additive gives a large influence on the performance of the catalyst.

Further, it has been made clear that in the Mo—Bi—Fe catalyst, when the temperature raising rate until the temperature reaches a calcination temperature in a calcination step is larger to some extent, there is a tendency that a catalyst having a higher catalyst performance is obtained.

The present inventors have completed the present invention based on the findings as described above.

That is, the present invention is as described below.

[1] A method for producing a catalyst, comprising:
a slurry preparation step of preparing a slurry comprising a Mo compound, an Fe compound, a Bi compound, and an additive having a decomposition temperature of 500° C. or less;
a drying step of drying the slurry to obtain a dried material; and
a calcination step of calcining the dried material to obtain a calcined material, wherein the calcination step comprises a step of raising temperature of a calcination atmosphere to a predetermined temperature, and a temperature raising rate is 10° C./min or less during a temperature of a calcination atmosphere equal to or lower than the decomposition temperature of the additive in the step.

[2] The method for producing the catalyst according to [1], wherein the temperature raising rate in the step of raising the temperature is 2° C./min or more.

[3] The method for producing the catalyst according to [1] or [2], wherein a gas in the calcination atmosphere is replaced with another gas in a gas replacing time of 180 seconds or less in the calcination step.

[4] The method for producing the catalyst according to any one of [1] to [3], wherein a molar ratio of Mo, Fe, and Bi in the slurry is 12:1.3 or more:0.5 or less.

[5] The method for producing the catalyst according to any one of [1] to [4], wherein the decomposition temperature of the additive is in a range of 100° C. to 400° C.

[6] The method for producing the catalyst according to any one of [1] to [5], wherein the additive is a carboxylic acid.

[7] A method for producing an unsaturated nitrile, comprising:
a step of obtaining a catalyst by the method according to any one of [1] to [6]; and
a step of bringing an olefin into contact with ammonia and molecular oxygen in a presence of the catalyst to produce the unsaturated nitrile.

Advantageous Effects of Invention

According to the method for producing a catalyst of the present invention, a catalyst giving a high unsaturated nitrile yield can be produced.

DESCRIPTION OF EMBODIMENT

Hereinafter, an embodiment for carrying out the present invention (hereinafter, simply referred to as "present embodiment") will be described, but the present invention is not limited to the present embodiment described below and can be modified variously within the scope thereof.

<Method for Producing Catalyst>

A method for producing a catalyst according to the present embodiment comprises: a step of preparing a slurry comprising a Mo compound, an Fe compound, a Bi compound, and an additive having a decomposition temperature of 500° C. or less; a drying step of drying the slurry to obtain a dried material; and a calcination step of calcining the dried material to obtain a calcined material, wherein a temperature raising rate near the decomposition temperature of the additive in the calcination step is adjusted to a particular range.

[1] Catalyst

The catalyst obtained by the production method according to the present embodiment contains a Mo element, a Bi element, and an Fe element, preferably has a composition containing 1.3 atoms or more of Fe and 0.5 atoms or less of Bi to 12 atoms of Mo, and is particularly suitable for use in the reaction of subjecting an olefin to gas-phase catalytic oxidation in the presence of ammonia.

Hereinafter, the composition, the shape, and the embodiment thereof will be described in more detail.

(1) Composition

The catalyst obtained by the production method according to the present embodiment preferably comprises Mo, Bi, and Fe as essential components and is preferably a composite oxide thereof.

Generally, it is understood that in a Mo—Bi—Fe catalyst, each metal element has a function described below. That is, Mo has a function as an adsorption site for an olefin such as propylene and as an activation site for ammonia to produce a NH species. Bi acts as an activation site for an olefin such as propylene and abstracts a hydrogen to produce a n allyl species. The iron contributes to transfer of oxygen from a gas phase to an active site by redox of $Fe^{3+}/Fe^{2+}$. These functions of respective metal elements in the catalyst is described in, for example, Grasselli, R. K., "Handbook of Heterogeneous Catalysis 5", J, Wiley VCH, 1997, p2302.

The content ratio of respective metal elements of Mo, Bi, and Fe in the catalyst is preferably such that 1.3 atoms or more of Fe and 0.5 atoms or less of Bi are contained to 12 atoms of Mo. For example, from the viewpoint of making the constitutional ratio of crystal phases proper for allowing the catalyst to exhibit catalytic functions, the content ratio is preferably such that 0.1 to 0.5 atoms of Bi and 1.4 to 2.5 atoms of Fe are contained to 12 atoms of Mo.

Examples of a metal component that may be contained if necessary in the catalyst besides Mo, Bi, and Fe include (a) at least one metal element selected from the group consisting of chromium and manganese, (b) at least one metal element selected from the group consisting of nickel, cobalt, and magnesium, (c) at least one metal element selected from the group consisting of sodium, potassium, rubidium, and cesium, and (d) at least one metal element selected from rare earth elements. It is inferred that among these, the metal element of (a) has a redox function in an oxide catalyst similarly to iron and enhances the high-temperature stability of the crystal phases in the main catalyst. It is inferred that the metal element of (b) dissolves and stabilizes $Fe^{2+}$ in an $M(II)MoO_4$ structure. It is inferred that the metal element of (c) covers acid centers at the surface of the catalyst to suppress side reactions. It has been considered that the metal element of (d) improves the high-temperature stability of the crystal phases of the main catalyst. It is considered that the catalyst performance is further improved due to these functions.

From the viewpoint of allowing the catalyst to exhibit the functions of respective metal elements more effectively and surely to further improve the catalyst performance, 0 to 3 atoms of the metal element of (a) is preferably contained, 4 to 12 atoms of the metal element of (b) is preferably contained, 0.01 to 2 atoms of the metal element of (c) is preferably contained, and 0.1 to 2 atoms of the metal element of (d) is preferably contained to 12 atoms of Mo in the catalyst. The catalyst may contain an element other than those described above.

(2) Shape

The particle shape of the catalyst obtained by the production method according to the present embodiment is not limited, but from the viewpoint such as making the fluidity in a reactor preferable, the particle shape of the catalyst is preferably spherical, and the surface thereof is preferably smooth.

(3) Carrier

In a case where production or the like of an unsaturated nitrile is industrially carried out, the production or the like is preferably carried out in a fluidized bed reactor. The catalyst for use in the fluidized bed reactor desirably has a sufficient strength, and therefore from such a viewpoint, the catalyst is preferably carried by a carrier.

Examples of the carrier include, but not particularly limited to, silica, alumina, titania, silica/alumina, and silica/titania. Among these, silica is preferable from the viewpoint of enhancing the yield of the unsaturated nitrile. Silica is preferably used as a carrier because in a case where the catalyst is used as a fluidized bed catalyst, the catalyst has a further excellent fluidity.

From the viewpoint of wear resistance, the content of the carrier is preferably 35% by mass or more based on the total amount of the catalyst and the carrier. From the viewpoint of obtaining a more sufficient catalytic activity and more satisfactory selectivity, the content of the carrier is preferably 60% by mass or less.

[2] Each Step in Method for Producing Catalyst

The method for producing a catalyst according to the present embodiment comprises: a slurry preparation step (step (i)) of preparing a slurry; a drying step (step (ii)) of drying the slurry to obtain a dried material; and a calcination step (step (iii)) of calcining the dried material to obtain a calcined material.

(1) Step (i)

The step (i) is a step of preparing a slurry to be a precursor of the catalyst and is a step of preparing a slurry comprising an additive having a decomposition temperature of 500° C. or less, a Mo compound, an Fe compound, and a Bi compound. The molar ratio of Mo, Fe, and Bi in the slurry is preferably 12:1.3 or more:0.5 or less. In a case where the catalyst is carried on a carrier, a component to be a supply source for the carrier may be mixed in this step (i).

For example, in the step (i), a solution containing the Mo compound to be a supply source for molybdenum is prepared, and this solution is thereafter mixed with the Fe compound, the Bi compound, an additional metal element, and, if necessary, a component to be a supply source for a carrier, and thus the slurry can be obtained. However, the order of adding respective compounds is not limited.

Hereinafter, the method for preparing the slurry will be described taking a case where the catalyst is provided with a silica carrier as an example, but the method for producing a catalyst according to the present embodiment is not limited to this.

The supply source (starting material) for each metal element, such as the Mo compound, the Fe compound, and the Bi compound, contained in the slurry is preferably a salt that is soluble to water or nitric acid. Examples of the supply sources for respective metal elements of molybdenum, bismuth, and iron, and the additional metal element that is further added if necessary to the catalyst include ammonium salts, nitrates, hydrochlorides, sulfates, organic acid salts, and inorganic acids which are soluble to water or nitric acid. Particularly, as the supply source for molybdenum, ammonium salts are preferable, and as the supply sources for bismuth, iron, and the additional metal element, nitrates of respective metal elements are preferable. The nitrates are also preferable in that they are easy to handle, and besides, they do not produce residue of chlorine that is produced in a case where a hydrochloride is used, or residue of sulfur that is produced in a case where a sulfate is used. Specific examples of the Mo compound, the Bi compound, and the Fe compound include ammonium paramolybdate, bismuth nitrate, and ferric nitrate, respectively. As the supply source for silica as a carrier, silica sol is suitable from the viewpoint of exhibiting the effects by the present invention more effectively and surely. Further, from the same viewpoint, the preferable concentration of silica in silica sol is 10 to 50% by mass. The concentration of an aqueous solution or the like to be added can also appropriately be adjusted so as to be a suitable concentration for spray-drying, which will be described later, of the slurry. The average primary particle diameter of silica contained in silica sol is not particularly limited. As the silica carrier, different types of silica sol each having a different average primary particle diameter may be mixed and used.

In the present embodiment, the slurry comprises an additive having a decomposition temperature of 500° C. or less besides the catalyst starting material and the carrier starting material. The additive is not particularly limited, and examples thereof include water-soluble polymers such as polyethylene glycol, polyvinyl alcohol, polyacrylic acid, polycarboxylic acids, polyacrylamide, and polyvinyl pyrrolidone; amines such as phenanthroline, ethanolamine, hydrazine, ethylenediamine, ethylenediaminetetraacetic acid, imidazole, pyridine, aniline, and pyrazole; amino acids such as glycine and glutamic acid; alcohols such as phenol, methanol, ethanol, and propanol; organic acids such as glycolic acid, malic acid, oxalic acid, tartaric acid, malonic acid, succinic acid, citric acid, lactic acid, salicylic acid, gallic acid, gluconic acid, maleic acid, and benzoic acid; and besides, phosphoric acid, acetylacetone, urea, thiourea, boric acid, acetone, dimethyl sulfoxide, iminodiacetic acid, nitrilotriacetic acid, diethylenetriaminepentaacetic acid, triethylenetraminehexaacetic acid, cyclohexane-1,2-diaminetetraacetic acid, N-hydroxyethylethylenediaminetriacetic acid, ethyleneglycoldiethyletherdiaminetetraacetic acid, and ethylenediaminetetrapropionic acid. The additive is preferably an additive having a decomposition temperature in the range of 100° C. to 400° C. The additive is more preferably an organic acid. The additive is still more preferably a carboxylic acid. These additives may be used singly, or two or more of these may be used together.

The upper limit of the content of the additive (in a case where two or more additives are contained, the total content thereof) is not particularly limited, but the additive is preferably contained so as to be 15% by mass or less based on the mass of the catalyst (in a case where a carrier is used, the total mass of the catalyst and the carrier) after calcination. By allowing the content of the additive to be 15% by mass or less, heat generation due to decomposition or diffusion of organic substances, or occurrence of cracking of the catalyst particle at a stage of producing the catalyst can be suppressed. The lower limit of the content of the additive is not particularly limited, but is preferably 0.5% by mass or more, more preferably 1 to 10% by mass, and still more preferably 1 to 5% by mass, based on the mass of the catalyst (in a case where a carrier is used, the total mass of the catalyst and the carrier) after calcination from the viewpoint of allowing the catalyst to exhibit the effects of the additive.

The additive can be added in the slurry by dissolving the additive in a solvent. On that occasion, the type of the solvent is not particularly limited, and examples thereof include an acid or water. Alternatively, the additive may be mixed with other starting materials in advance.

In the preparation of the slurry, the order of mixing respective supply sources is not particularly limited. As one example, the additive is added to silica sol while the silica sol is stirred, an aqueous solution containing the Mo compound is subsequently added, and a liquid in which a supply source for the metal element other than molybdenum, for example, the Fe compound or the Bi compound (preferably, a nitrate salt), is dissolved in an aqueous medium (preferably, a nitric acid aqueous solution) is subsequently added.

(2) Step (ii)

The step (ii) in the method for producing a catalyst according to the present embodiment is a step of drying the above-described slurry to obtain a dried material.

The drying method in the present step is not limited, and, for example, the dried material which is a spherical, fine particle suitable for fluidized bed reaction can be obtained by spray-drying the slurry. As a spray-drying apparatus, a general apparatus such as a rotary disk type or nozzle type apparatus can be used, and by adjusting operational conditions, a catalyst having a desired particle diameter can be obtained. A preferred particle diameter as a fluidized bed catalyst is an average particle diameter of 25 to 180 µm. One example of the spray-drying for obtaining a catalyst particle having a preferred particle diameter includes spray drying performed using a centrifugal nebulization apparatus (for example, OC-16 spray drier manufactured by Ohkawara Kakohki Co., Ltd.) provided with a dish type rotor installed at the center of the upper portion of a drier, and holding the temperature of air at the inlet of the drier at 180° C. to 250° C. and the temperature at the outlet at 100° C. to 150° C.

(3) Step (iii)

The step (iii) in the method for producing the catalyst according to the present embodiment is a step of calcining the dried material (for example, dried particle obtained by spray drying) obtained in the step (iii) to obtain a calcined material. The step (iii) comprises at least a step of raising temperature of a calcination atmosphere to a predetermined temperature (hereinafter, referred to as "first calcination step"), and a temperature raising rate is 10° C./min or less during a temperature of a calcination atmosphere equal to or lower than the decomposition temperature of the additive in the step. The temperature raising rate is more preferably 10° C./min or less until the temperature of the calcination atmosphere reaches the decomposition temperature of the additive +30° C.

This step (iii) preferably comprises at least two stages comprising a second calcination step described below in addition to the first calcination step from the viewpoint of more easily obtaining the above-described catalyst.

Hereinafter, each step will be described in detail.

[A] First Calcination Step

The first calcination step is a step of raising the temperature of the calcination atmosphere from room temperature or the drying temperature (in a case where calcination is performed subsequently after drying or other cases) in the step (ii) to a predetermined temperature (calcination temperature) set within the range of preferably 500° C. to 700°

C. The time for raising the temperature is preferably 1 hour or more, more preferably 1 to 10 hours, and still more preferably 3 to 7 hours. On this occasion, the temperature raising rate is not necessarily constant, but is preferably 2° C./min or more, more preferably 4° C./min or more, still more preferably 5° C./min or more, and further still more preferably 5.5° C./min or more. On the other hand, the temperature raising rate is 10° C./min or less at least at the temperature of the calcination atmosphere equal to or lower than the decomposition temperature of the additive. In a case where two types or more of such additives are contained in the slurry, the decomposition temperature of the additive (additive having a decomposition temperature of 500° C. or less) herein is defined as the highest temperature among the decomposition temperatures of respective additives.

The temperature raising rate at a temperature equal to or lower than the decomposition temperature of the additive is preferably 9° C./min or less, more preferably 7.5° C./min or less, and still more preferably 6° C./min or less.

According to an investigation conducted by the present inventors, it has been found out that by controlling the temperature raising rate in this way, a catalyst having a high catalytic efficiency (for example, a catalyst giving a high unsaturated nitrile yield) can be produced. It is considered that by allowing the temperature raising rate at a temperature equal to or lower than the decomposition temperature of the additive to be 10° C./min or less, cracks of the calcined material (catalyst) due to rapid decomposition of the additive are suppressed to prevent ununiform mixing of the calcined material during the calcination, so that calcination unevenness and the like can be reduced and a catalyst having a high catalytic efficiency is obtained. However, the mechanism is not limited to this.

Further, it has also been found out that when the temperature raising rate in raising the temperature to a predetermined temperature in the first calcination step is set to 2° C./min or more, there is a tendency that a catalyst having a high catalytic efficiency is obtained. It is considered that this is because in a case where the temperature is raised at a sufficient rate during the calcination, the dried material is not exposed to a decomposition gas from starting material nitric acid or the additive for a long time, and therefore occurrence of deviation in the metal composition (particularly, Fe and Mo) due to dissolution of Mo, Fe, and Bi is prevented. However, the mechanism is not limited to this.

Gradual combustion of components contained in the supply sources for respective metal elements, the components left in the above-described dried material (for example, dried particle), for example, nitric acid derived from ammonium nitrate or a metal nitrate, is another object of the first calcination step, and the upper limit value of the temperature raising rate in the temperature range other than the decomposition temperature region is not particularly limited.

[B] Second Calcination Step

The calcination step according to the present embodiment preferably comprises a second calcination step of holding a first calcined particle obtained in the first calcination step at a calcination temperature of, for example, 500° C. to 700° C. in addition to the first calcination step. The object of the second calcination step is to allow a crystal to grow. From such a viewpoint, the holding time at the calcination temperature in the second calcination step is preferably 0.5 to 15 hours, more preferably 2 to 10 hours, and still more preferably 2 to 6 hours. The holding time is preferably adjusted from the viewpoint of preventing deterioration of activity due to a decrease in the specific surface area of the catalyst.

In the present embodiment, the calcination step may appropriately comprise further step or steps besides the first and the second calcination steps.

In the calcination step according to the present embodiment, the gas in the calcination atmosphere is desirably replaced with another gas such as air or an inert gas from the viewpoint of removing gases produced by decomposition of the nitrates as the starting materials and the additive during the calcination. By allowing the gas in the calcination atmosphere to be replaced quickly, redissolution of the metal components during the calcination can be suppressed. The method for replacing the gas in the calcination atmosphere is not limited, replacing the gas can be performed by, for example, supplying a replacing gas (air or inert gas), and on that occasion, an intake of the gas to be replaced is preferably performed at the same time. Alternatively, the gas in the calcination atmosphere may be replaced with the air outside by performing an intake (discharge) of the gas in a calcination kiln to make the inside of the calcination kiln negative pressure, thereby taking in the air outside.

The gas in the calcination atmosphere is preferably replaced in 180 seconds or less (the time for replacing the gas in the calcination atmosphere is 180 seconds or less), more preferably 90 seconds or less, and still more preferably 60 seconds or less.

The time for replacing the gas in the calcination atmosphere herein refers to time until the volume in the calcination kiln is filled with the replacing gas, and, for example, in a case where replacing the gas is performed by supplying the replacing gas, is expressed by V/Q (sec.) when the volume of the calcination kiln is assumed to be V cm$^3$ and the flow rate of the supply gas is assumed to be Q cm$^3$/sec. For example, in a case where the volume of the kiln is 400 cm$^3$ and the amount of air to be supplied is 400 cm$^3$/min, the time for replacing the gas will be 60 seconds (1 minute).

Replacing the gas in the calcination atmosphere may be performed at any timing in the calcination step, the number of times of replacing the gas is not limited, and for example, in a case where the above-described second calcination step is included in the calcination step, replacing the gas may be performed in any of the first calcination step and the second calcination step, may be performed in both of them, and is preferably performed at all times at least in the first calcination step, more preferably performed at all times through the calcination step.

In the present embodiment, the catalyst comprising Mo, Bi, and Fe can be obtained through the steps described above.

Next, a method for producing an unsaturated nitrile using this catalyst will be described.

<Method for Producing Unsaturated Nitrile>

The method for producing an unsaturated nitrile according to the present embodiment comprises: a step of obtaining a catalyst by the above-described method for producing a catalyst; and a step of bringing an olefin into contact with ammonia and oxygen in a presence of the catalyst (subjecting the olefin to gas-phase catalytic ammoxidation reaction with ammonia and oxygen) to produce the unsaturated nitrile.

Specifically, the method produces an unsaturated nitrile such as acrylonitrile or methacrylonitrile by, for example, reacting an olefin such as propylene or isobutene with ammonia and molecular oxygen using the catalyst (namely, gas-phase catalytic ammoxidation reaction). As a reactor, a fluidized bed reactor is preferably used.

The olefin, such as propylene, and ammonia each being a starting material in the ammoxidation reaction are not necessarily of high purity, and the olefin and ammonia of industrial grade can also be used. As an oxygen source for molecular oxygen, air is usually used. The volume ratio of ammonia and air to the olefin such as propylene is preferably in the range of 1:0.9 to 1.7:7 to 11, more preferably in the range of 1:1.0 to 1.5:8 to 10 in terms of olefin:ammonia:air.

The reaction temperature is preferably in the range of 400 to 460° C., more preferably in the range of 410 to 440° C. The reaction pressure is preferably in the range of normal pressure to 3 atm. The contact time between the mixed gas of starting materials comprising an olefin, ammonia, and molecular oxygen, and the catalyst is preferably 1 to 8 seconds, more preferably 2 to 6 seconds.

According to the present embodiment, a high unsaturated nitrile yield can be given (an unsaturated nitrile can be produced at a high yield).

EXAMPLES

Hereinafter, the present embodiment will be described more specifically giving Examples, but the present embodiment is not limited to these Examples at all. Methods for evaluating various physical properties are as described below.

(Method for Measuring Decomposition Temperature of Additive)

A differential thermal balance (TG-DTA) was used for measuring the decomposition temperature of the additive. Analytical conditions are as described below.

[Apparatus]

Product name "Thermo plus EVO2", manufactured by Rigaku Corporation

[Measurement Conditions]

Sample pan: Platinum pan, Standard specimen: $Al_2O_3$, Air atmosphere (Method for Measuring Time for Replacing Gas)

The time during which the gas in the calcination atmosphere was replaced was calculated as time until the volume in the calcination kiln was filled by supplying or discharging, or supplying and discharging air or an inert gas.

(Conditions for Producing Unsaturated Nitrile Trough Ammoxidation Reaction of Propylene and Yield of Unsaturated Nitrile)

Acrylonitrile was produced through ammoxidation reaction of propylene using each catalyst obtained in Examples and Comparative Examples. A Pyrex® glass pipe having an inner diameter of 25 mm, the glass pipe having 16 10-mesh wire nets built-in at an interval of 1 cm, was used as a reaction pipe to be used on that occasion.

The reaction was performed setting the amount of the catalyst to 50 cc, the reaction temperature to 430° C., and the reaction pressure to 0.17 MPa and supplying a propylene/ammonia/oxygen mixed gas to the glass pipe. On that occasion, the content of propylene in the mixed gas was set to 9% by volume, and the volume ratio of ammonia to propylene was set such that a sulfuric acid unit requirement defined by the following expression was 20±2 kg/T-AN. The volume ratio of oxygen to propylene was set such that an oxygen concentration of a gas at the outlet of the reactor was 0.2±0.02% by volume.

The contact time defined by the following expression was changed by changing the flow rate of the mixed gas, and the contact time was set such that the conversion rate of propylene, the conversion rate defined by the following expression, was thereby 99.3±0.2%.

The yield of acrylonitrile produced through the reaction was determined as a value defined by the following expression.

$$\text{Sulfuric acid unit requirement}(kg/T - AN) = \frac{\text{Weight of sulfuric acid needed to neutralize unreacted ammonia}(kg)}{\text{Weight of acrylontrile produced}(T)}$$ [Expression 1]

$$\text{Contact time(sec.)} = \frac{\text{Amount of catalyst}(cc)}{\text{Flow rate of mixed gas}(cc - NTP/\text{sec.})} \times \frac{273}{273 + \text{reaction temperature}(° C.)} \times \frac{\text{Reaction pressure(MPa)}}{0.10}$$

$$\text{Conversion rate of propylene(\%)} = \frac{\text{Propylene consumed(mol)}}{\text{Propylene supplied(mol)}} \times 100$$

$$\text{Acrylonitrile yield(\%)} = \frac{\text{Acrylonitrile produced(mol)}}{\text{Propylene supplied(mol)}} \times 100$$

Example 1

An oxide catalyst in which an oxide having a composition represented by $Mo_{12.00}Bi_{0.38}Ce_{0.80}Co_{4.30}Fe_{1.55}Ni_{3.20}Rb_{0.12}$ was carried on 40% by mass of silica based on the total amount of the oxide and silica was prepared in the manner as described below.

To 1333.3 g of silica sol containing 30% by mass of $SiO_2$, 25.0 g of oxalic acid dihydrate (purity of 99.5%, decomposition temperature: 190° C.) dissolved in 200 g of water was added. The silica-oxalic acid mixed liquid was mixed at 0.2 kW/m³ and 40° C. for 10 minutes. Subsequently, to the silica-oxalic acid mixed liquid, 480.9 g of ammonium paramolybdate $[(NH_4)_6Mo_7O_{24} \cdot 4H_2O]$ dissolved in 858.4 g of water was added under stirring, and further 42.4 g of bismuth nitrate $[Bi(NO_3)_3 \cdot 5H_2O]$, 142.9 g of iron nitrate $[Fe(NO_3)_3 \cdot 9H_2O]$, 287.0 g of cobalt nitrate $[Co(NO_3)_2 \cdot 6H_2O]$, 211.2 g of nickel nitrate $[Ni(NO_3)_2 \cdot 6H_2O]$, 78.9 g of cerium nitrate $[Ce(NO_3)_3 \cdot 6H_2O]$, and 4.02 g of rubidium nitrate $[RbNO_3]$ dissolved in 392.4 g of 16.6% by mass of nitric acid were added to prepare a slurry.

Subsequently, the slurry was dried using a rotary disk type spray drier to obtain a dried particle. On that occasion, the temperature of air at the inlet of the drier was set to 230° C., and the temperature of air at the outlet was set to 110° C. The number of revolutions of the disk was set to 12500 revolutions/min.

The dried particle thus obtained was transferred into a kiln and was calcined in an air atmosphere. Specifically, the temperature was first raised from room temperature to 480° C. at 2° C./min and from 480° C. to 540° C. at 1.5° C./min, and then held at 540° C. for 4 hours to obtain an oxide catalyst. Air was supplied into the kiln during the calcination such that the time for replacing the gas in the calcination atmosphere was 60 seconds.

Example 2

A dried particle was obtained in the same manner as in Example 1. The resulting dried particle was transferred into the kiln and was calcined in an air atmosphere. Specifically, the temperature was first raised from room temperature to 160° C. at 2° C./min, from 160° C. to 220° C. at 5° C./min, from 220° C. to 480° C. at 2° C./min, and from 480° C. to 540° C. at 1.5° C./min, and then held at 540° C. for 4 hours to obtain an oxide catalyst. Air was supplied into the kiln during the calcination such that the time for replacing the gas in the calcination atmosphere was 60 seconds.

Example 3

A dried particle was obtained in the same manner as in Example 1. The resulting dried particle was transferred into the kiln and was calcined in an air atmosphere. Specifically, the temperature was first raised from room temperature to 160° C. at 2° C./min, from 160° C. to 220° C. at 5.7° C./min, from 220° C. to 480° C. at 2° C./min, and from 480° C. to 540° C. at 1.5° C./min, and then held at 540° C. for 4 hours to obtain an oxide catalyst. Air was supplied into the kiln during the calcination such that the time for replacing the gas in the calcination atmosphere was 60 seconds.

Example 4

A dried particle was obtained in the same manner as in Example 1. The resulting dried particle was transferred into the kiln and was calcined in an air atmosphere. Specifically, the temperature was first raised from room temperature to 160° C. at 2° C./min, from 160° C. to 220° C. at 10° C./min, from 220° C. to 480° C. at 2° C./min, and from 480° C. to 540° C. at 1.5° C./min, and then held at 540° C. for 4 hours to obtain an oxide catalyst. Air was supplied into the kiln during the calcination such that the time for replacing the gas in the calcination atmosphere was 60 seconds.

Example 5

A dried particle was obtained in the same manner as in Example 1 except that the amount of oxalic acid dihydrate was changed to 50.0 g. The resulting dried particle was transferred into the kiln and was calcined in an air atmosphere. Specifically, the temperature was first raised from room temperature to 160° C. at 2° C./min, from 160° C. to 220° C. at 5° C./min, from 220° C. to 480° C. at 2° C./min, and from 480° C. to 540° C. at 1.5° C./min, and then held at 540° C. for 4 hours to obtain an oxide catalyst. Air was supplied into the kiln during the calcination such that the time for replacing the gas in the calcination atmosphere was 60 seconds.

Example 6

A dried particle was obtained in the same manner as in Example 1 except that the type of the additive was changed to tartaric acid (decomposition temperature: 170° C.). The resulting dried particle was transferred into the kiln and was calcined in an air atmosphere. Specifically, the temperature was first raised from room temperature to 140° C. at 2° C./min, from 140° C. to 200° C. at 5° C./min, from 200° C. to 480° C. at 2° C./min, and from 480° C. to 540° C. at 1.5° C./min, and then held at 540° C. for 4 hours to obtain an oxide catalyst. Air was supplied into the kiln during the calcination such that the time for replacing the gas in the calcination atmosphere was 180 seconds.

Example 7

A dried particle was obtained in the same manner as in Example 1. The resulting dried particle was transferred into the kiln and was calcined in an air atmosphere. Specifically, the temperature was first raised from room temperature to 160° C. at 1° C./min, from 160° C. to 220° C. at 5° C./min, from 220° C. to 480° C. at 1° C./min, and from 480° C. to 540° C. at 1.5° C./min, and then held at 540° C. for 4 hours to obtain an oxide catalyst. Air was supplied during the calcination such that the time for replacing the gas in the calcination atmosphere was 60 seconds.

Example 8

An oxide catalyst in which an oxide having a composition represented by $Mo_{12.00}Bi_{0.40}Ce_{0.60}Co_{3.80}Fe_{1.60}Ni_{3.10}Mg_{0.80}Rb_{0.12}$ was carried on 40% by mass of silica based on the total amount of the oxide and silica was prepared in the manner as described below.

To a mixture of 666.7 g of aqueous silica sol containing 30% by mass of $SiO_2$ having an average particle diameter of primary particles of 12 nm and 666.7 g of aqueous silica sol containing 30% by mass of $SiO_2$ having an average particle diameter of primary particles of 41 nm, 25.0 g of oxalic acid dihydrate (purity of 99.5%) dissolved in 200 g of water was added. The silica-oxalic acid mixed liquid was mixed at 0.2 kW/m$^3$ and 40° C. for 10 minutes. Subsequently, to the silica-oxalic acid mixed liquid, 487.7 g of ammonium paramolybdate $[(NH_4)_6Mo_7O_{24}.4H_2O]$ dissolved in 870.6 g of water was added under stirring, and further 45.3 g of bismuth nitrate $[Bi(NO_3)_3.5H_2O]$, 149.6 g of iron nitrate $[Fe(NO_3)_3.9H_2O]$, 257.2 g of cobalt nitrate $[Co(NO_3)_2.6H_2O]$, 207.5 g of nickel nitrate $[Ni(NO_3)_2.6H_2O]$, 60.0 g of cerium nitrate $[Ce(NO_3)_3.6H_2O]$, 47.2 g of magnesium nitrate $[Mg(NO_3)_2.6H_2O]$, and 4.08 g of rubidium nitrate $[RbNO_3]$ dissolved in 395.1 g of 16.6% by mass of nitric acid were added to prepare a slurry.

Subsequently, the slurry was dried using a rotary disk type spray drier to obtain a dried particle. On that occasion, the temperature of air at the inlet of the drier was set to 230° C., and the temperature of air at the outlet was set to 110° C. The number of revolutions of the disk was set to 12500 revolutions/min.

The dried particle thus obtained was transferred into the kiln and was calcined in an air atmosphere. Specifically, the temperature was first raised from room temperature to 480° C. at 2° C./min and from 480° C. to 540° C. at 1.5° C./min, and then held at 540° C. for 4 hours to obtain an oxide catalyst. Air was supplied into the kiln during the calcination such that the time for replacing the gas in the calcination atmosphere was 60 seconds.

Example 9

An oxide catalyst in which an oxide having a composition represented by $Mo_{12.00}Bi_{0.48}Ce_{0.92}Fe_{1.75}Ni_{5.00}Mg_{2.00}Rb_{0.12}$ was carried on 40% by mass of silica based on the total amount of the catalyst was prepared in the manner as described below.

To a mixture of 666.7 g of aqueous silica sol containing 30% by mass of $SiO_2$ having an average particle diameter of primary particles of 12 nm and 666.7 g of aqueous silica sol containing 30% by mass of $SiO_2$ having an average particle diameter of primary particles of 41 nm, 25.0 g of oxalic acid dihydrate (purity of 99.5%) dissolved in 200 g of water was added. The silica-oxalic acid mixed liquid was mixed at 0.2 kW/m$^3$ and 40° C. for 10 minutes. Subsequently, to the silica-oxalic acid mixed liquid, 489.8 g of ammonium paramolybdate $[(NH_4)_6Mo_7O_{24}.4H_2O]$ dissolved in 874.4 g of water was added under stirring, and further 53.8 g of bismuth nitrate [Bi(NO$_3$)$_3$.5H$_2$O], 163.5 g of iron nitrate [Fe(NO$_3$)$_3$.9H$_2$O], 336.2 g of nickel nitrate [Ni(NO$_3$)$_2$.6H$_2$O], 92.4 g of cerium nitrate [Ce(NO$_3$)$_3$.6H$_2$O], 118.5 g of magnesium nitrate [Mg(NO$_3$)$_2$.6H$_2$O], and 4.09 g of rubidium nitrate [RbNO$_3$] dissolved in 395.5 g of 16.6% by mass of nitric acid were added to prepare a slurry.

Subsequently, the slurry was dried using a rotary disk type spray drier to obtain a dried particle. On that occasion, the temperature of air at the inlet of the drier was set to 230° C., and the temperature of air at the outlet was set to 110° C. The number of revolutions of the disk was set to 12500 revolutions/min.

The dried particle thus obtained was transferred into the kiln and was calcined in an air atmosphere. Specifically, the temperature was first raised from room temperature to 480° C. at 2° C./min and from 480° C. to 540° C. at 1.5° C./min, and then held at 540° C. for 4 hours to obtain an oxide catalyst. Nitrogen was supplied into the kiln during the calcination such that the time for replacing the gas in the calcination atmosphere was 90 seconds.

Example 10

An oxide catalyst was obtained in the same manner as in Example 1 except that the time for replacing the gas in the calcination atmosphere was changed to 30 seconds.

Example 11

An oxide catalyst was obtained in the same manner as in Example 1 except that the time for replacing the gas in the calcination atmosphere was changed to 210 seconds.

Example 12

An oxide catalyst was obtained in the same manner as in Example 1 except that the time for replacing the gas in the calcination atmosphere was changed to 240 seconds.

Example 13

A dried particle was obtained in the same manner as in Example 1. The resulting dried particle was transferred into the kiln and was calcined in an air atmosphere. Specifically, the temperature was first raised from room temperature to 160° C. at 2° C./min, from 160° C. to 220° C. at 1.5° C./min, from 220° C. to 480° C. at 2° C./min, and from 480° C. to 540° C. at 1.5° C./min, and then held at 540° C. for 4 hours to obtain an oxide catalyst. Air was supplied into the kiln during the calcination such that the time for replacing the gas in the calcination atmosphere was 60 seconds.

Example 14

A dried particle was obtained in the same manner as in Example 1 except that the additive was changed to tartaric acid. The resulting dried particle was transferred into the kiln and was calcined in an air atmosphere. Specifically, the temperature was first raised from room temperature to 140° C. at 2° C./min, from 140° C. to 200° C. at 1.5° C./min, from 200° C. to 480° C. at 2° C./min, and from 480° C. to 540° C. at 1.5° C./min, and then held at 540° C. for 4 hours to obtain an oxide catalyst. Air was supplied into the kiln during the calcination such that the time for replacing the gas in the calcination atmosphere was 180 seconds.

Example 15

A dried particle was obtained in the same manner as in Example 9. The resulting dried particle was transferred into the kiln and was calcined in an air atmosphere. Specifically, the temperature was first raised from room temperature to 160° C. at 2° C./min, from 160° C. to 220° C. at 1.5° C./min, from 220° C. to 480° C. at 2° C./min, and from 480° C. to 535° C. at 1.5° C./min, and then held at 535° C. for 4 hours to obtain an oxide catalyst. Nitrogen was supplied into the kiln during the calcination such that the time for replacing the gas in the calcination atmosphere was 90 seconds.

Comparative Example 1

A dried particle was obtained in the same manner as in Example 1. The resulting dried particle was transferred into the kiln and was calcined in an air atmosphere. Specifically, the temperature was first raised from room temperature to 160° C. at 2° C./min, from 160° C. to 220° C. at 12° C./min, from 220° C. to 480° C. at 2° C./min, and from 480° C. to 540° C. at 1.5° C./min, and then held at 540° C. for 4 hours to obtain an oxide catalyst. Air was supplied into the kiln during the calcination such that the time for replacing the gas in the calcination atmosphere was 60 seconds.

Comparative Example 2

A dried particle was obtained in the same manner as in Example 1 except that the additive was changed to tartaric acid. The resulting dried particle was transferred into the kiln and was calcined in an air atmosphere. Specifically, the temperature was first raised from room temperature to 140° C. at 2° C./min, from 140° C. to 200° C. at 12° C./min, from 200° C. to 480° C. at 2° C./min, and from 480° C. to 540° C. at 1.5° C./min, and then held at 540° C. for 4 hours to obtain an oxide catalyst. Air was supplied into the kiln during the calcination such that the time for replacing the gas in the calcination atmosphere was 180 seconds.

Comparative Example 3

A dried particle was obtained in the same manner as in Example 9. The resulting dried particle was transferred into the kiln and was calcined in an air atmosphere. Specifically, the temperature was first raised from room temperature to 160° C. at 2° C./min, from 160° C. to 220° C. at 12° C./min, from 220° C. to 480° C. at 2° C./min, and from 480° C. to 535° C. at 1.5° C./min, and then held at 535° C. for 4 hours to obtain an oxide catalyst. Nitrogen was supplied into the kiln during the calcination such that the time for replacing the gas in the calcination atmosphere was 90 seconds.

TABLE 1

| | Composition | Additive | Amount of additive per catalyst (wt %) | AN yield (%) | Temperature raising rate (° C./min) | Time for replacing gas during calcination (sec.) |
|---|---|---|---|---|---|---|
| Example 1 | $Mo_{12.00}Bi_{0.38}Ce_{0.80}Fe_{1.55}Co_{4.30}Ni_{3.20}Rb_{0.12}$ | Oxalic acid | 2.5 | 84.2 | 2.0 | 60 |
| Example 2 | $Mo_{12.00}Bi_{0.38}Ce_{0.80}Fe_{1.55}Co_{4.30}Ni_{3.20}Rb_{0.12}$ | Oxalic acid | 2.5 | 84.2 | 5.0 | 60 |
| Example 3 | $Mo_{12.00}Bi_{0.38}Ce_{0.80}Fe_{1.55}Co_{4.30}Ni_{3.20}Rb_{0.12}$ | Oxalic acid | 2.5 | 84.3 | 5.7 | 60 |
| Example 4 | $Mo_{12.00}Bi_{0.38}Ce_{0.80}Fe_{1.55}Co_{4.30}Ni_{3.20}Rb_{0.12}$ | Oxalic acid | 2.5 | 84.2 | 10.0 | 60 |
| Example 5 | $Mo_{12.00}Bi_{0.38}Ce_{0.80}Fe_{1.55}Co_{4.30}Ni_{3.20}Rb_{0.12}$ | Oxalic acid | 5.0 | 84.3 | 5.0 | 60 |
| Example 6 | $Mo_{12.00}Bi_{0.38}Ce_{0.80}Fe_{1.55}Co_{4.30}Ni_{3.20}Rb_{0.12}$ | Tartaric acid | 2.5 | 84.1 | 5.0 | 180 |
| Example 7 | $Mo_{12.00}Bi_{0.38}Ce_{0.80}Fe_{1.55}Co_{4.30}Ni_{3.20}Rb_{0.12}$ | Oxalic acid | 2.5 | 84.1 | 5.0 | 60 |
| Example 8 | $Mo_{12.00}Bi_{0.40}Ce_{0.60}Fe_{1.60}Co_{3.80}Ni_{3.10}Mg_{0.80}Rb_{0.12}$ | Oxalic acid | 2.5 | 84.7 | 2.0 | 60 |
| Example 9 | $Mo_{12.00}Bi_{0.48}Ce_{0.92}Fe_{1.75}Ni_{5.00}Mg_{2.00}Rb_{0.12}$ | Oxalic acid | 2.5 | 83.6 | 2.0 | 90 |
| Example 10 | $Mo_{12.00}Bi_{0.38}Ce_{0.80}Fe_{1.55}Co_{4.30}Ni_{3.20}Rb_{0.12}$ | Oxalic acid | 2.5 | 84.2 | 2.0 | 30 |
| Example 11 | $Mo_{12.00}Bi_{0.38}Ce_{0.80}Fe_{1.55}Co_{4.30}Ni_{3.20}Rb_{0.12}$ | Oxalic acid | 2.5 | 83.8 | 2.0 | 210 |
| Example 12 | $Mo_{12.00}Bi_{0.38}Ce_{0.80}Fe_{1.55}Co_{4.30}Ni_{3.20}Rb_{0.12}$ | Oxalic acid | 2.5 | 83.7 | 2.0 | 240 |
| Example 13 | $Mo_{12.00}Bi_{0.38}Ce_{0.80}Fe_{1.55}Co_{4.30}Ni_{3.20}Rb_{0.12}$ | Oxalic acid | 2.5 | 83.9 | 1.5 | 60 |
| Example 14 | $Mo_{12.00}Bi_{0.38}Ce_{0.80}Fe_{1.55}Co_{4.30}Ni_{3.20}Rb_{0.12}$ | Tartaric acid | 2.5 | 83.9 | 1.5 | 180 |
| Example 15 | $Mo_{12.00}Bi_{0.48}Ce_{0.92}Fe_{1.75}Ni_{5.00}Mg_{2.00}Rb_{0.12}$ | Oxalic acid | 2.5 | 83.5 | 1.5 | 90 |
| Comparative Example 1 | $Mo_{12.00}Bi_{0.38}Ce_{0.80}Fe_{1.55}Co_{4.30}Ni_{3.20}Rb_{0.12}$ | Oxalic acid | 2.5 | 83.7 | 12.0 | 60 |
| Comparative Example 2 | $Mo_{12.00}Bi_{0.38}Ce_{0.80}Fe_{1.55}Co_{4.30}Ni_{3.20}Rb_{0.12}$ | Tartaric acid | 2.5 | 83.8 | 12.0 | 180 |
| Comparative Example 3 | $Mo_{12.00}Bi_{0.48}Ce_{0.92}Fe_{1.75}Ni_{5.00}Mg_{2.00}Rb_{0.12}$ | Oxalic acid | 2.5 | 83.3 | 12.0 | 90 |

As can been seen from the results shown in Table 1, it was confirmed that the oxide catalyst obtained by the production method according to the present embodiment can produce an unsaturated nitrile at a high yield through gas-phase catalytic ammoxidation reaction of an olefin.

INDUSTRIAL APPLICABILITY

The present invention can be utilized for producing a catalyst comprising Mo, Bi, and Fe, and can suitably be utilized particularly in producing an oxide catalyst to be used in producing an unsaturated nitrile by reacting an olefin with molecular oxygen and ammonia, or in producing an unsaturated aldehyde or a conjugated diolefin by reacting an olefin with molecular oxygen.

The present application is based on a Japanese Patent Application (Japanese Patent Application No. 2017-138362) filed with Japan Patent Office on Jul. 14, 2017, the contents of which are incorporated herein by reference.

The invention claimed is:

1. A method for producing a catalyst, comprising:
   a slurry preparation step of preparing a slurry comprising a Mo compound, an Fe compound, a Bi compound, and an additive having a decomposition temperature of 500° C. or less;
   a drying step of drying the slurry to obtain a dried material; and
   a calcination step of calcining the dried material to obtain a calcined material,
   wherein the calcination step comprises a step of raising temperature of a calcination atmosphere to a predetermined temperature, and a temperature raising rate is 10° C./min or less during a temperature of a calcination atmosphere equal to or lower than the decomposition temperature of the additive in the step,
   the predetermined temperature is 500° C. to 700° C., and
   the method further comprising a step of replacing a gas in the calcination atmosphere with air in a gas replacing time of 180 seconds or less in the calcination step.

2. The method for producing the catalyst according to claim 1, wherein the temperature raising rate in the step of raising the temperature is 2° C./min or more.

3. The method for producing the catalyst according to claim 1, wherein the gas replacing time is 90 seconds or less in the calcination step.

4. The method for producing the catalyst according to claim 1, wherein a molar ratio of Mo, Fe, and Bi in the slurry is 12:1.3 or more:0.5 or less.

5. The method for producing the catalyst according to claim 1, wherein the decomposition temperature of the additive is in a range of 100° C. to 400° C.

6. The method for producing the catalyst according to claim 1, wherein the additive is a carboxylic acid.

7. A method for producing an unsaturated nitrile, comprising:
   a step of obtaining a catalyst by the method according to claim 1; and
   a step of bringing an olefin into contact with ammonia and molecular oxygen in a presence of the catalyst to produce the unsaturated nitrile.

* * * * *